US011872298B2

(12) United States Patent
Santos et al.

(10) Patent No.: US 11,872,298 B2
(45) Date of Patent: *Jan. 16, 2024

(54) COSMETIC USE OF ARTHROFACTIN

(71) Applicant: L'OREAL, Paris (FR)

(72) Inventors: Luiz Santos, Aulnay-sous-Bois (FR); Lucie Tournier-Couturier, Aulnay-sous-Bois (FR); Nakako Shibagaki, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/471,720

(22) PCT Filed: Dec. 22, 2017

(86) PCT No.: PCT/EP2017/084556
§ 371 (c)(1),
(2) Date: Jun. 20, 2019

(87) PCT Pub. No.: WO2018/115522
PCT Pub. Date: Jun. 28, 2018

(65) Prior Publication Data
US 2020/0022894 A1    Jan. 23, 2020

(30) Foreign Application Priority Data

Dec. 22, 2016 (FR) ..................... 16 63253

(51) Int. Cl.
| *A61K 8/64* | (2006.01) |
| *A61K 8/99* | (2017.01) |
| *A61K 8/06* | (2006.01) |
| *A61Q 19/00* | (2006.01) |
| *A61K 47/54* | (2017.01) |
| *A61K 38/12* | (2006.01) |
| *A61K 31/20* | (2006.01) |
| *C07K 7/64* | (2006.01) |
| *C07K 14/195* | (2006.01) |
| *C07K 1/107* | (2006.01) |

(52) U.S. Cl.
CPC ................ *A61K 8/64* (2013.01); *A61K 8/062* (2013.01); *A61K 8/99* (2013.01); *A61K 38/12* (2013.01); *A61K 47/542* (2017.08); *A61Q 19/007* (2013.01); *A61K 31/20* (2013.01); *A61K 2800/85* (2013.01); *C07K 1/1077* (2013.01); *C07K 7/64* (2013.01); *C07K 14/195* (2013.01)

(58) Field of Classification Search
CPC .... A61K 2800/85; A61K 31/20; A61K 38/12; A61K 47/542; A61K 8/0295; A61K 8/062; A61K 8/64; A61K 8/99; A61Q 19/007; C07K 14/195; C07K 1/1077; C07K 7/64
USPC ....................................... 514/18.8
See application file for complete search history.

(56) References Cited

FOREIGN PATENT DOCUMENTS

| CN | 1303267 A | 7/2001 |
| FR | 2 898 049 A1 | 9/2007 |
| FR | 3 016 291 A1 | 7/2015 |
| JP | H10 59832 A | 3/1998 |
| WO | WO 99/62482 A1 | 12/1999 |

OTHER PUBLICATIONS

Final Report on the Safety Assessment of Ethyl Acetate and Butyl Acetate,, Journal of the American College of Toxicology, vol. 8, No. 4,1989 Mary Ann Liebert, Inc., Publishers.*
Stablizers, Thickeners and Gelling agents, Food&nutrition handout, published 2017, pp. 1-4.*
Lange et al., "Predicting the Structure of Cyclic Lipoproperties by Bioinformatics: Structure Revision of Arthrofactin", ChemBioChem, 2012, 13, 2671-2675.
Morikawa et al., "A New Lipopeptide Biosurfactant Produced by *Arthrobacter* sp. Strain MIS38", Journal of Bacteriology, Oct. 1993, 175 (20), 6459-6466.
Balibar et al., "Generation of D Amino Acid Residues in Assembly of Arthrofactin by Dual Condensation/Epimerization Domains", Chemistry & Biology, Nov. 2005, 12, 1189-1200.
Washio et al., "Identification and Characterization of the Genes Responsible for the Production of the Cyclic Lipopeptide Arthrofactin by *Pseudomonas* sp. MIS38", Bioscience, Biotechnology, and Biochemistry, 2010, 74 (5), 992-999.

* cited by examiner

*Primary Examiner* — Julie Ha
*Assistant Examiner* — Erinne R Dabkowski
(74) *Attorney, Agent, or Firm* — POLSINELLI PC

(57) ABSTRACT

The present invention relates to the non-therapeutic cosmetic use of a mixture of arthrofactins as a moisturizer particularly for the skin, mucosa and particularly dry skin.

16 Claims, No Drawings

COSMETIC USE OF ARTHROFACTIN

CROSS REFERENCE TO RELATED APPLICATIONS

This application is a National Phase filing under 35 U.S.C. § 371 of PCT/EP2017/084556 filed on 22 Dec. 2017; which application in turn claims priority to Application No. 16 63253 filed in France on 22 Dec. 2016. The entire contents of each application are hereby incorporated by reference.

The present invention relates to the use of a mixture of arthrofactins in the domain of care of keratinic materials such as the skin, and particularly as a moisturizing agent for keratinic materials, preferably the skin.

The invention also relates to a cosmetic treatment method for keratinic materials, particularly the skin, comprising application on said materials, of a cosmetic composition comprising at least one mixture of arthrofactins as described below.

The present invention further relates to a cosmetic treatment method making use of a mixture of arthrofactins as described below, particularly to moisturize the skin. Acting as a barrier for protection and exchange with the environment, the skin is both resistant and fragile, it can lose its suppleness and its ability to retain water can reduce; thus causing dryness of the skin, exacerbated particularly after the age of 65 years.

It is known that the Stratum Corneum or corneal layer that is the outermost surface zone of the epidermis, intervenes particularly in moisturization of the skin. Located at the interface with the external environment, its function is particularly to delay excessive loss of water from deeper layers of the epidermis. The Stratum Corneum also provides protection against mechanical aggression. It also forms the first defense against UV radiation.

It is 10 μm thick and is composed of corneocytes stacked vertically and surrounded by a matrix of membranes enriched in lipids. It is thus a system with two compartments that can be compared with a wall of bricks composed of a nuclear cells and intercellular lamellar membranes. Due to this compact stratified structure, the Stratum Corneum performs its barrier function by opposing the transcutaneous loss of water. It thus makes an efficient contribution to moisturization of the skin, via its ability to capture and retain water located principally in the intercellular spaces.

For obvious reasons, it is important to guarantee a sufficient moisturization level of the skin to maintain its suppleness, its softness, tonicity and/or its appearance.

Molecular players involved in moisturization of the skin include particularly:
  The sodium channel of the apical membrane of epithelial cells, called ENaC, for Epithelial Na Channel, is responsible for the transport of sodium through the epithelium and involves proteins SCNN1A, SCNN1 D, NEDD4L and STXBP1, among others.
  Aquaporins such as AQP3 and AQP9 that form "pores" permeable to molecules of water in the biological membranes. Aquaporins enable the passage of water from one side of the membrane to the other while preventing ions from penetrating into the cell.
  Hyaluronic acid, synthesized from the Hyaluronate Synthetase enzyme or Hyaluronic Acid Synthetase (HAS) HAS3. In vitro studies prove that hyaluronic acid stimulates the synthesis of proteins forming tight junctions such as occludins or preventing insensible water losses. Furthermore, hyaluronic acid increases natural moisturization of the skin (Clinical trial report: clinical efficacy evaluation of tree moisturizing products in improvement of moisture content of the skin. Ellead skin research center Co., Ltd. Nov. 27, 2006).
  Proteins involved in creation of the corneal envelope such as TGM5, LCE3D, FLG2, SPRR1A and CNFN and cells involved in the synthesis of lipids such as ELOVL3 and FADS2 which enable limiting water losses by favoring reinforcement of the barrier function.

All of these players favor the capture and retention of water.

In general, a reduction in the moisturization level can be prevented or treated by acting on the Stratum Corneum via active agents called moisturizers such as for example urea and glycerol that are reference agents in this field.

However, undesirable side effects are observed with these two types of active agents.

Indeed, urea can strongly modify the skin barrier by increasing Insensible Water Loss (IWL), which significantly reduces the barrier function of the Stratum Corneum.

Glycerol has the disadvantage that it makes formulas sticky when it is used at a high concentration.

Therefore there is a need to find other active agents in the domain of skin moisturization that do not have the disadvantages mentioned above.

Furthermore, since consumers tend to mistrust chemically synthesized compounds used in cosmetic compositions, there is an additional interest in having cosmetically active biotechnologically derived biomolecules. However, very few biomolecules of this type have been disclosed until now, particularly for the cosmetic treatment of dry skins.

The present invention is the result of the unexpected finding by the inventors that arthrofactin, a partially cyclic lipopeptide from the biosurfactants family described in Lange et al. (2012) *ChemBioChem* 13:2671-2675 and produced by *Pseudomonas* sp MIS 38 (Morikawa et al. (1993) *J. Bacteriol.* 175:6459-6466), and more particularly a mixture of arthrofactins produced by *Pseudomonas* sp MIS 38, activates the synthesis of genes associated with moisturization in these cells, demonstrating a moisturizing effect on keratinic materials and particularly the skin.

The mixture of arthrofactins produced by *Pseudomonas* sp MIS 38 as described below enables having compositions with good stability and/or remaining pleasant for the consumer, in other words not very sticky, pleasant to touch, and/or not displaying uncomfortable sensations such as tightness, while having a moisturizing effect.

The inventors have discovered that the mixture of arthrofactins produced by *Pseudomonas* sp MIS 38 as described below was a good moisturizing agent, and in particular had a beneficial effect in terms of elasticity of the Stratum corneum and/or improves the barrier function.

Patent FR2898049 discloses a cosmetic process for lips care comprising application onto the lipds of a composition comprising an oil in a polar phase emulsion, said emulsion comprising at least one cyclic lipopeptide likely to be obtained by fermentation of procaryotes, the cyclic lipopeptide acting as an emulsifier to stabilize the emulsion. However, this document does not describe any moisturizing property of arthrofactin.

International application WO9962482 discloses a surfactant for use in the external preparation of the skin comprising a lipopeptide derived from procaryotes and having a low penetration power into the skin and a low irritation power for the skin. However, this document does not describe any moisturizing property of arthrofactin.

In the context of the present invention, the term "keratinic materials" refers to preferably human keratinic materials and particularly the skin (preferably human skin) and its appendages.

"Skin" refers to face skin and/or body skin, or the scalp.

The cutaneous zone may be chosen in particular from among:

the hands, the face, in particular the forehead, cheeks, or eye contour (periocular region), and in particular crow's feet, the area below the eye (eyebag), or the eyelids, the neck, the feet, the legs, the arms and forearms and preferably face skin.

"Appendages" means eyelashes, eyebrows, nails and hair, and particularly eyelashes and hair.

According to one particular embodiment of the invention, the cosmetic composition comprising at least arthrofactin or a mixture of arthrofactins as described below is intended for topical administration on keratinic materials such as the skin and particularly human skin.

Therefore an object of the present invention is a cosmetic composition intended for topical application on the keratinic materials and particularly the skin, and comprising as active ingredient, a mixture of arthrofactins comprising:

(i) arthrofactin A of the following formula (I):

$$R_1\text{-D-Leu}_1\text{-D-Asp}_2\text{-D-allo-Thr}_3\text{-D-Leu}_4\text{-D-Leu}_5\text{-D-Ser}_6\text{-L-Leu}_7\text{-D-Ser}_8\text{-L-Ile}_9\text{-L-Ile}_{10}\text{-L-Asp}_{11} \quad (I),$$

wherein the hydroxyl group of the D-allo-Thr$_3$ amino acid residue forms an ester bond with the C-terminal carboxyl group of the L-Asp amino acid residue, and R$_1$ represents the group of the following formula (I'):

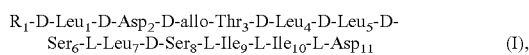

(I')

wherein R$_1$' is a saturated alkyl chain with 5 to 8 carbon atoms, and (ii) at least one derivative of arthrofactin A, said derivative being of the following formula (II):

$$\text{R-Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11} \quad (II)$$

wherein

Xaa$_1$, Xaa$_4$, Xaa$_5$, Xaa$_7$, Xaa$_9$ and Xaa$_{10}$ each independently represent D-Leu, L-Leu, D-Ile or L-Ile, Xaa$_2$ and Xaa$_{11}$ each independently represent D-Asp, L-Asp, D-Glu or L-Glu, Xaa$_3$ represents D-Thr, L-Thr, D-allo-Thr or L-allo-Thr, Xaa$_6$ and Xaa$_8$ each independently represent D-Ser, L-Ser, D-Gln or L-Gln, the hydroxyl group of the Xaa$_3$ amino acid residue forms an ester bond with the C-terminal carboxyl group of the Xaa$_{11}$ amino acid residue, and R represents the group of the following formula (II'):

(II')

wherein R' is a hydrocarbon chain with 5 to 9 carbon atoms, optionally comprising at least one ethylene unsaturation with a cis or trans configuration;

the composition further comprising a physiologically acceptable medium.

Another object of the present invention is a cosmetic composition intended for topical application on keratinic materials and particularly the skin, and comprising, as active ingredient, a mixture of arthrofactins comprising:

(i) arthrofactin A of the following formula (I):

$$R_1\text{-D-Leu}_1\text{-D-Asp}_2\text{-D-allo-Thr}_3\text{-D-Leu}_4\text{-D-Leu}_5\text{-D-Ser}_6\text{-L-Leu}_7\text{-D-Ser}_8\text{-L-Ile}_9\text{-L-Ile}_{10}\text{-L-Asp}_{11} \quad (I),$$

wherein the hydroxyl group of the D-allo-Thr$_3$ amino acid residue forms an ester bond with the C-terminal carboxyl group of the L-Asp amino acid residue, and R$_1$ represents the group of the following formula (I'):

(I')

wherein R$_1$' is a saturated alkyl chain with 5 to 8 carbon atoms, and (ii) at least one derivative of arthrofactin A, said derivative being of the following formula (II):

$$\text{R-Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11} \quad (II)$$

wherein

Xaa$_1$, Xaa$_4$, Xaa$_5$, Xaa$_7$, Xaa$_9$ and Xaa$_{10}$ each independently represent D-Leu, L-Leu, D-Ile or L-Ile, Xaa$_2$ and Xaa$_{11}$ each independently represent D-Asp, L-Asp, D-Glu or L-Glu, Xaa$_3$ represents D-Thr, L-Thr, D-allo-Thr or L-allo-Thr, Xaa$_6$ and Xaa$_8$ each independently represent D-Ser, L-Ser, D-Gln or L-Gln, the hydroxyl group of the Xaa$_3$ amino acid residue forms an ester bond with the C-terminal carboxyl group of the Xaa$_{11}$ amino acid residue, and R represents the group of the following formula (II'):

(II')

wherein R' is a hydrocarbon chain with 5 to 9 carbon atoms, optionally comprising at least one ethylene unsaturation with a cis or trans configuration;

the composition further comprising a physiologically acceptable medium and at least one compound chosen among thickeners, preservatives, perfumes, bactericides, pigments, dyes, organic solvents such as particularly $C_1$-$C_6$ alcohols and $C_2$-$C_{10}$ carboxylic acid esters, carbon and/or silicone oils of inorganic, animal and/or plant origin, waxes, fillers, emulsifiers, co-emulsifiers, UVA and/or UVB light protection agents also called UV filters, polymers, hydrophilic or lipophilic gelling agents.

According to one particular embodiment, the object of this invention is a cosmetic composition intended for topical application on the keratinic materials and particularly the skin, and comprising, as active ingredient, a mixture of arthrofactins comprising:
(i) arthrofactin A of formula (I) as described above, and:
(ii) at least one derivative of arthrofactin A, said derivative being of formula (II) as described above,
the composition further comprising a physiologically acceptable medium and at least one compound chosen among thickeners, preservatives, perfumes, bactericides, organic solvents such as particularly $C_1$-$C_6$ alcohols and $C_2$-$C_{10}$ carboxylic acid esters, carbon and/or silicone oils with inorganic, animal and/or plant origin.

This invention also relates to a non-therapeutic cosmetic treatment method comprising the application of a mixture of arthrofactins as defined above on keratinic materials, particularly on the skin and more particularly on dry skin.

Another object of the invention relates to non-therapeutic cosmetic use of a mixture of arthrofactins as defined above, as moisturizer for keratinic materials, particularly the skin, mucosa, and particularly for the treatment of dry skin.

The mixture of arthrofactins as defined below, or the compositions comprising such a mixture, can be used once or repeatedly, for example 1 to 2 times per day, preferably over a period of at least one week, and more particularly at least 4 weeks.

DETAILED DESCRIPTION OF THE INVENTION

The active ingredient of the composition according to the invention, having particularly the moisturizing properties described herein, is a mixture of arthrofactins comprising:
(i) arthrofactin A of the following formula (I):

$R_1$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$  (I), wherein
the hydroxyl group of the D-allo-Thr$_3$ amino acid residue forms an ester bond with the C-terminal carboxyl group of the L-Asp amino acid residue, and
$R_1$ represents the group of the following formula (I'):

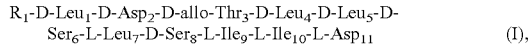

(I')

wherein $R_1'$ is a saturated alkyl chain with 5 to 8 carbon atoms, particularly with 7 carbon atoms, and
(ii) at least one derivative of arthrofactin A, said derivative being of the following formula (II):

R-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$  (II)

wherein
Xaa$_1$, Xaa$_4$, Xaa$_5$, Xaa$_7$, Xaa$_9$ and Xaa$_{10}$ each independently represent D-Leu, L-Leu, D-Ile or L-Ile,
Xaa$_2$ and Xaa$_{11}$ each independently represent D-Asp, L-Asp, D-Glu or L-Glu,
Xaa$_3$ represents D-Thr, L-Thr, D-allo-Thr or L-allo-Thr,
Xaa$_6$ and Xaa$_8$ each independently represent D-Ser, L-Ser, D-Gln or L-Gln,
the hydroxyl group of the Xaa$_3$ amino acid residue forms an ester bond with the C-terminal carboxyl group of the Xaa$_{11}$ amino acid residue, and
R represents the group of the following formula (II'):

(II')

wherein R' is a hydrocarbon chain with 5 to 9 carbon atoms, optionally comprising at least one ethylene unsaturation with a cis or trans configuration.

In the context of the invention, amino acids preceded by the "D-" symbol are D configuration amino acids, while amino acids preceded by the "L-" symbol are L configuration amino acids.

The term "D-allo-Thr" designates the stereoisomer of threonine with a (2R,3R) configuration while the term "L-allo-Thr" designates the stereoisomer of threonine with a (2S,3S) configuration.

"Alkyl chain" means herein a saturated hydrocarbon chain.

In one particular embodiment, the $R_1'$ group as defined above is an alkyl chain with 5, 6, 7, or 8 carbon atoms and preferably an alkyl chain with 7 carbon atoms.

In one particular embodiment, the R' group as defined above is a hydrocarbon chain with 5, 6, 7, 8 or 9 carbon atoms, optionally comprising at least one ethylene unsaturation with a cis or trans configuration. In one particular embodiment, the R' group is a saturated alkyl chain with 5, 6, 7, 8 or 9 carbon atoms. In another embodiment, the R' group is a hydrocarbon chain with 5, 6, 7, 8, or 9 carbon atoms comprising at least one ethylene unsaturation with a cis or trans configuration, preferably comprising exactly one ethylene unsaturation with a cis or trans configuration.

In one particular embodiment, the R' group is a n alkyl chain with 7 or 9 carbon atoms, optionally comprising at least one ethylene unsaturation with a cis or trans configuration. In one particular embodiment, the R' group is a saturated alkyl chain with 7 or 9 carbon atoms. In another embodiment, the R' group is an alkyl chain with 7 or 9 carbon atoms comprising at least one ethylene unsaturation with a cis or trans configuration, preferably comprising exactly one ethylene unsaturation with a cis or trans configuration.

In one particular embodiment, the R' group is a saturated alkyl chain with 7 carbon atoms. In another particular embodiment, the R' group is a hydrocarbon chain with 7 carbon atoms comprising at least one ethylene unsaturation with a cis or trans configuration, preferably comprising exactly one ethylene unsaturation with a cis or trans configuration.

In another particular embodiment, the R' group is a saturated alkyl chain with 9 carbon atoms. In another particular embodiment, the R' group is a hydrocarbon chain with 9 carbon atoms comprising at least one ethylene unsaturation with a cis or trans configuration, preferably comprising exactly one ethylene unsaturation with a cis or trans configuration.

In one particular embodiment, the $Xaa_1$, $Xaa_4$, $Xaa_5$, $Xaa_7$, $Xaa_9$ and $Xaa_{10}$ amino acids as described above each independently represent D-Leu or L-Leu. In one particular embodiment, the $Xaa_1$, $Xaa_4$, $Xaa_5$, $Xaa_7$, $Xaa_9$ and $Xaa_{10}$ amino acids each independently represent D-Ile or L-Ile.

In another embodiment, the $Xaa_1$, $Xaa_4$ and $Xaa_5$ amino acids each independently represent D-Leu or D-Ile. In another particular embodiment, the $Xaa_7$, $Xaa_9$ and $Xaa_{10}$ amino acids each independently represent L-Leu or L-Ile.

In one preferred embodiment, the $Xaa_1$, $Xaa_4$ and $Xaa_5$ amino acids each represent D-Leu. In another preferred embodiment, the $Xaa_7$ amino acid represents L-Leu. In another preferred embodiment, the $Xaa_9$ and $Xaa_{10}$ amino acids each represent L-Ile.

In one particularly preferred embodiment, the $Xaa_1$, $Xaa_4$ and $Xaa_5$ amino acids each represent D-Leu, the $Xaa_7$ amino acid represents L-Leu, and the $Xaa_9$ and $Xaa_{10}$ amino acids each represent L-Ile.

In one particular embodiment, the $Xaa_2$ and $Xaa_{11}$ amino acids each independently represent D-Asp or L-Asp. In another particular embodiment, the $Xaa_2$ and $Xaa_{11}$ amino acids each independently represent D-Glu or L-Glu. In another particular embodiment, the $Xaa_2$ and $Xaa_{11}$ amino acids each independently represent D-Asp or D-Glu. In one preferred embodiment, the $Xaa_2$ amino acid represents D-Asp. In one preferred embodiment, the $Xaa_{11}$ amino acid represents L-Asp or L-Glu. In one even more preferred embodiment, the $Xaa_2$ amino acid represents D-Asp and the Xaa amino acid represents L-Asp or L-Glu.

In one particular embodiment, the $Xaa_3$ amino acid represents D-Thr or L-Thr. In another particular embodiment, the $Xaa_3$ amino acid represents D-allo-Thr or L-allo-Thr. In another particular embodiment, the $Xaa_3$ amino acid represents D-Thr or D-allo-Thr. In one preferred embodiment, the $Xaa_3$ amino acid represents D-allo-Thr.

In one particular embodiment, the $Xaa_6$ and $Xaa_8$ amino acids each independently represent D-Ser or L-Ser. In another particular embodiment, the $Xaa_6$ and $Xaa_8$ amino acids each independently represent D-Gln or L-Gln. In another embodiment, the $Xaa_6$ and $Xaa_8$ amino acids each independently represent D-Ser or D-Gln. In one preferred embodiment, the $Xaa_6$ and $Xaa_8$ amino acids each represent D-Ser.

Thus, in one particular embodiment, the at least one derivative of arthrofactin A is of the following formula (II):

$$R\text{-}Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} \quad (II)$$

wherein
$Xaa_1$, $Xaa_4$, $Xaa_5$, $Xaa_7$, $Xaa_9$ and $Xaa_{10}$ each independently represent D-Leu, L-Leu, D-Ile or L-Ile,
$Xaa_2$ and $Xaa_{11}$ each independently represent D-Asp, L-Asp, D-Glu or L-Glu,
$Xaa_3$ represents D-Thr, L-Thr, D-allo-Thr or L-allo-Thr,
$Xaa_6$ and $Xaa_8$ each independently represent D-Ser, L-Ser, D-Gln or L-Gln,
the hydroxyl group of the $Xaa_3$ amino acid residue forms an ester bond with the C-terminal carboxyl group of the Xaa amino acid residue, and R represents the group of the following formula (II'):

wherein R' is a saturated alkyl chain with 7 carbon atoms, a hydrocarbon chain with 7 carbon atoms comprising exactly one ethylene unsaturation with a cis or trans configuration, a saturated alkyl chain with 9 carbon atoms, or a hydrocarbon chain with 9 carbon atoms comprising exactly one ethylene unsaturation with a cis or trans configuration.

In another particular embodiment, the at least one derivative of arthrofactin A has the following formula (II):

$$R\text{-}Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} \quad (II)$$

wherein
$Xaa_1$, $Xaa_4$, $Xaa_5$, $Xaa_7$, $Xaa_9$ and $Xaa_{10}$ each independently represent D-Leu, L-Leu, D-Ile or L-Ile,
$Xaa_2$ and $Xaa_{11}$ each independently represent D-Asp, L-Asp, D-Glu or L-Glu,
$Xaa_3$ represents D-Thr, L-Thr, D-allo-Thr or L-allo-Thr,
$Xaa_6$ and $Xaa_8$ each independently represent D-Ser, L-Ser, D-Gln or L-Gln,
the hydroxyl group of the $Xaa_3$ amino acid residue forms an ester bond with the C-terminal carboxyl group of the Xaa amino acid residue, and
R represents the group of the following formula (II'):

wherein R' is a saturated alkyl chain with 7 carbon atoms, a saturated alkyl chain with 9 carbon atoms, or a hydrocarbon chain with 9 carbon atoms comprising exactly one ethylene unsaturation with a cis or trans configuration.

In another particular embodiment, the at least one derivative of arthrofactin A is of the following formula (II):

$$R\text{-}Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} \quad (II)$$

wherein
$Xaa_1$, $Xaa_4$ and $Xaa_5$ each represent D-Leu, $Xaa_7$ represents L-Leu, and $Xaa_9$ and $Xaa_{10}$ each represent L-Ile,
$Xaa_2$ represents D-Asp and $Xaa_{11}$ represents L-Asp or L-Glu,
$Xaa_3$ represents D-allo-Thr,
$Xaa_6$ and $Xaa_8$ each represent D-Ser,
the hydroxyl group of the $Xaa_3$ amino acid residue forms an ester bond with the C-terminal carboxyl group of the $Xaa_{11}$ amino acid residue, and R represents the group of the following formula (II'):

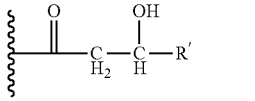
(II')

wherein R' is an alkyl chain with 5 to 9 carbon atoms, optionally comprising at least one ethylene unsaturation with a cis or trans configuration.

In another particular embodiment, the at least one derivative of arthrofactin A is of the following formula (II):

R-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$ (II)

wherein

Xaa$_1$, Xaa$_4$ and Xaa$_5$ each represent D-Leu, Xaa$_7$ represents L-Leu, and Xaa$_9$ and Xaa$_{10}$ each represent L-Ile, Xaa$_2$ represents D-Asp and Xaa$_{11}$ represents L-Asp or L-Glu, Xaa$_3$ represents D-allo-Thr, Xaa$_6$ and Xaa$_8$ each represent D-Ser, the hydroxyl group of the Xaa$_3$ amino acid residue forms an ester bond with the C-terminal carboxyl group of the Xaa$_{11}$ amino acid residue, and R represents the group of the following formula (II'):

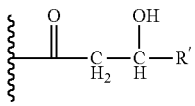
(II')

wherein R' is a saturated alkyl chain with 7 carbon atoms, a saturated alkyl chain with 9 carbon atoms, or a hydrocarbon chain with 9 carbon atoms comprising exactly one ethylene unsaturation with a cis or trans configuration.

In one particular embodiment, said at least one derivative of arthrofactin A is chosen from the group consisting in arthrofactin B, arthrofactin C, arthrofactin D and mixtures thereof, arthrofactin B being of the following formula (III):

R$_1$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Glu$_{11}$ (III), wherein the hydroxyl group of the D-allo-Thr$_3$ amino acid residue forms an ester bond with the C-terminal carboxyl group of the L-Glu$_{11}$ amino acid residue, and R$_1$ represents the group of the following formula (I'):

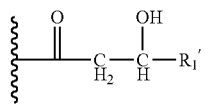
(I')

wherein R$_1$' is a saturated alkyl chain with 5 to 8 carbon atoms;

arthrofactin C being of the following formula (IV):

R$_2$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp (IV), wherein the hydroxyl group of the D-allo-Thr$_3$ amino acid residue forms an ester bond with the C-terminal carboxyl group of the L-Asp$_{11}$ amino acid residue, and R$_2$ represents the group of the following formula (IV'):

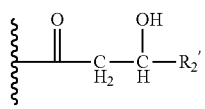
(IV')

wherein R$_2$' is an alkyl chain with 9 carbon atoms, comprising exactly one unsaturation;

arthrofactin D being of the following formula (V):

R$_3$-D-Leu$_1$-D-Asp$_2$-D-allo-Thr$_3$-D-Leu$_4$-D-Leu$_5$-D-Ser$_6$-L-Leu$_7$-D-Ser$_8$-L-Ile$_9$-L-Ile$_{10}$-L-Asp$_{11}$ (V), wherein the hydroxyl group of the D-allo-Thr$_3$ amino acid residue forms an ester bond with the C-terminal carboxyl group of the L-Asp amino acid residue, and R$_3$ represents the group of the following formula (V'):

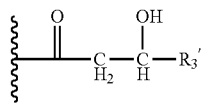
(V')

wherein R$_3$$^1$ is a saturated alkyl chain with 9 carbon atoms.

According to one particular embodiment of the invention, the active ingredient of the composition according to the invention, having particularly the moisturizing properties described herein, is a mixture of arthrofactins comprising:

(i) arthrofactin A of the following formula (IA):

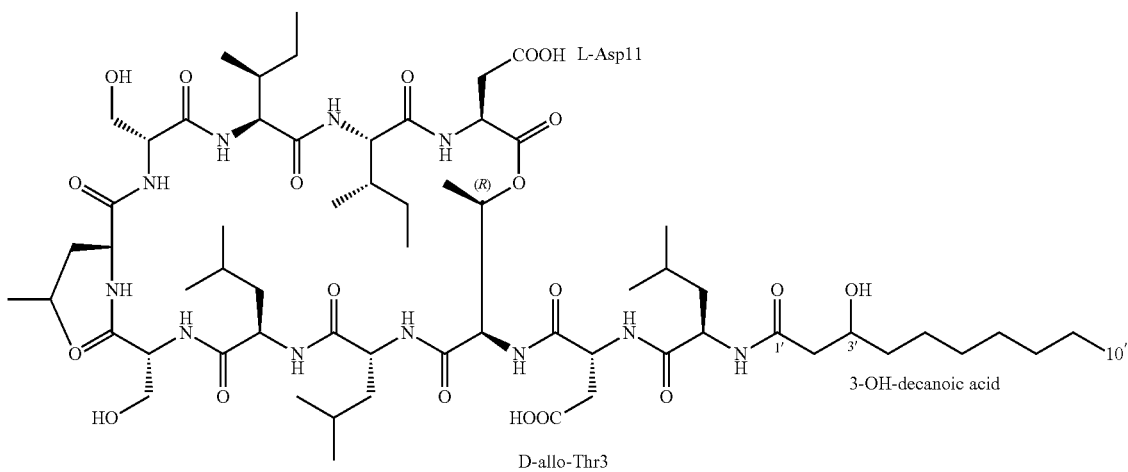

(ii) at least one derivative of arthrofactin A, said derivative being of the following formula (IIA) and/or (IIB) and/or (IIC):

mixture of arthrofactins, particularly the group composed of arthrofactin A and derivatives of arthrofactin A as defined above.

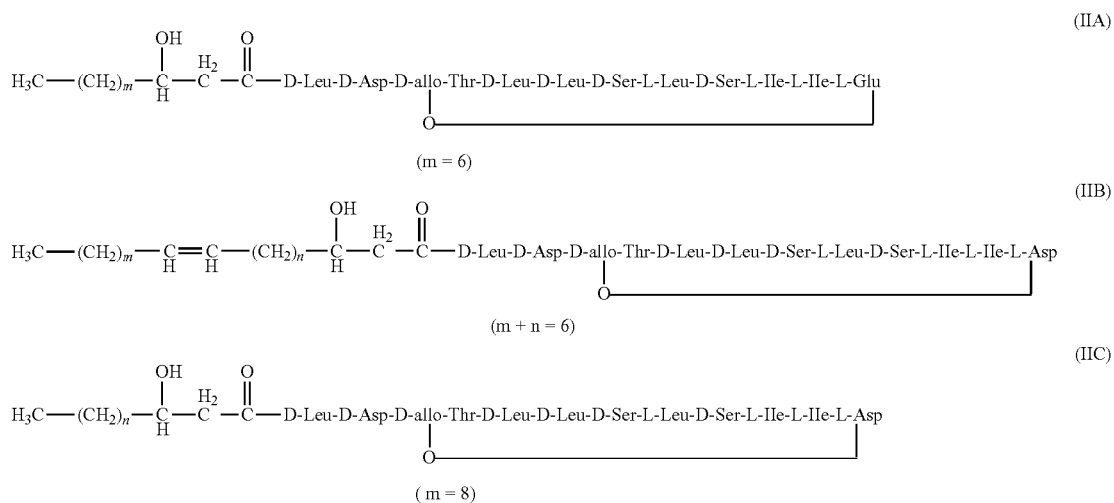

According to one particular embodiment of the invention, the active ingredient of the composition according to the invention, having particularly the moisturizing properties described herein, is a mixture of arthrofactins comprising:

(i) arthrofactin A of formula (IA)
(ii) a derivative of arthrofactin A of formula (IIA)
(iii) a derivative of arthrofactin A of formula (IIB)
(iv) a derivative of arthrofactin A of formula (IIC)

The R, $R_1$, $R_2$ and $R_3$ groups as defined above are bound to the N-terminal end of the $1^{st}$ amino acid (D-Leu$_1$ or Xaa$_1$) of the peptide sequence defined above.

In one particularly preferred embodiment of the invention, the mixture of arthrofactins according to the invention mostly comprises arthrofactin A.

By "mostly comprises arthrofactin A" is meant herein that arthrofactin A represents at least 50% by weight, preferably at least 60%, preferably at least 70% by weight of the The inventors have demonstrated that the mixture of arthrofactins as defined above was typically obtained by fermentation with the *Pseudomonas* sp. strain MIS38.

Thus, in one particular embodiment, the mixture of arthrofactins according to the invention is likely to be obtained by fermentation with the *Pseudomonas* sp strain MIS38.

The *Pseudomonas* sp strain MIS38 is well known to those skilled in the art and is for example described in Morikawa et al. (1993) *J. Bacteriol.* 175:6459-6466.

The mixture of arthrofactins according to the invention can be obtained by fermentation with the *Pseudomonas* sp. strain MIS38, using any fermentation technique well known to the skilled person, for example using the fermentation technique described in Washio et al. (2010) *Biosci. Biotechnol. Biochem.* 74:992-999. Typically, the *Pseudomonas* sp. strain MIS38 can be cultivated in LB medium (1% Bactotryptone, 0.5% yeast extract, 0.5% NaCl, pH 7.2) at 30° C.

during 48 h. The culture can then be centrifuged and the supernatant recovered and concentrated, for example by ultrafiltration. The mixture of arthrofactins can then be purified from this supernatant by extraction in the solid phase or liquid-liquid extraction.

The mixture of arthrofactins according to the invention can be obtained particularly using the method described in ChemBioChem, 2012, 13, 2671-2675.

Composition

The composition according to the invention is particularly a cosmetic composition.

The mixture of arthrofactins according to the invention can be present in cosmetic compositions according to the invention in a quantity that can be between 0.01 and 10% by weight, preferably between 0.1 and 5% by weight, preferably between 0.5 and 3% by weight, even more preferably between 1 and 2% by weight, relative to the total weight of the composition.

The composition further comprises a physiologically acceptable medium, preferably a cosmetically acceptable medium, in other words odorless, colorless and with no unpleasant appearance, and that does not generate any discomfort such as tingling or tightness unacceptable to the user. In particular, the composition is adapted to topical application on the skin.

"Physiologically acceptable medium" thus means a medium compatible with keratinic materials of human beings, in particular with body or face skin.

The composition according to the invention can include any cosmetic additives usually used in the envisaged application field.

The invention also relates to a composition comprising a mixture of arthrofactins as defined above and one or several additional moisturizers different from arthrofactin of formula (I) and its arthrofactin derivatives of formula (II), in a physiologically acceptable medium.

Preferably, the additional moisturizers are chosen among glycerol, urea, hydroxyethyl urea, hyaluronic acid, propanediol, threhalose, mannitol, xylitol, sorbitol, glycine, β-alanine, taurine, trimethyl glycine, and polyethylene glycol (PEG) derivatives.

Another object of the invention is a cosmetic method for moisturization of keratinic materials, particularly the skin, comprising or consisting in applying one of the compositions as defined above, on a keratinic material, preferably on the skin. Preferably, the keratinic materials such as the skin are human keratinic materials.

Dosage Forms

These compositions in which the compounds used according to the invention can be implemented are useful in particular for non-therapeutic care of the skin. They are particularly useful to moisturize the skin, particularly for the treatment of dry skin.

They can demonstrate their efficiency for non-therapeutic care treatment of the skin, namely for preventive purposes. They can also be used for non-therapeutic treatment of the skin after the appearance of skin moisturization disorders.

A composition used according to the invention is advantageously adapted for topical application on the skin.

This composition can be a care composition. Preferably, it is a skin care composition.

For a topical application on the skin, a composition according to the invention may be in any of the dosage forms conventionally used for this type of application and particularly in the form of aqueous gels, aqueous or hydroalcoholic solutions. They may also, by the addition of a fatty or oil phase, be in the form of dispersions such as lotion, emulsions of liquid or semi-liquid consistency such as milk, obtained by dispersing a fatty phase in an aqueous phase (O/W) or conversely (W/O), or suspensions or emulsions of soft, semi-solid or solid consistency such as cream or gel, or multiple emulsions (W/O/W or O/W/O), microemulsions, ionic and/or non-ionic type vesicle dispersions, or wax/aqueous phase dispersions. These compositions are prepared using usual methods.

Aqueous Phase

The compositions according to the invention intended for cosmetic use may comprise at least one aqueous phase. They are formulated particularly in aqueous lotions or in a water-in-oil emulsion, an oil-in-water emulsion, or in a multiple emulsion (triple oil-in-water-in-oil or water-in-oil-in-water emulsion) (such emulsions are known and described for example by C. FOX in "Cosmetics and Toiletries"—November 1986—Vol 101—pages 101-112).

The aqueous phase of said compositions contains water and generally other solvents soluble in water or miscible with water. Solvents that are soluble or miscible in water comprise short-chain mono alcohols, for example in $C_1$-$C_4$ such as ethanol, isopropanol; diols or polyols.

The compositions according to the invention preferably have a pH ranging from 3 to 9 depending on the substrate chosen.

When the composition(s) is (are) in the form of emulsion, it (they) generally contain(s) one several emulsifying surfactants, depending on the nature of the emulsion.

The total quantity of emulsifiers in the composition(s) according to the invention shall preferably be at contents in active material ranging between 1 and 8% by weight and more particularly between 2 and 6% by weight relative to the total weight of the composition.

Fatty Phase

The compositions according to the invention may contain at least one organic liquid phase non-miscible in water, known as a fatty phase. This generally includes one or several hydrophobic compounds rendering said phase non-miscible in water. Said phase is liquid (in the absence of a structuring agent) at room temperature (20-25° C.). Preferentially, the organic liquid phase non-miscible in water according to the invention generally comprises at least one volatile oil and/or one non-volatile oil and optionally at least one structuring agent.

"Oil" herein means a fatty body that is liquid at room temperature (25° C.) and atmospheric pressure (760 mm Hg namely $1.05 \times 10^5$ Pa). The oil may be volatile or non-volatile.

In the context of the invention, the term "volatile oil" denotes oil capable of evaporating on contact with the keratinic material, such as the skin, in less than an hour at room temperature and at atmospheric pressure. Volatile oils according to the invention are volatile cosmetic oils that are liquid at room temperature, having a vapor pressure different from zero at room temperature and atmospheric pressure, particularly ranging from 0.13 Pa to 40,000 Pa ($10^{-3}$ to 300 mm Hg), particularly ranging from 1.3 Pa to 13,000 Pa (0.01 to 100 mm Hg), and more particularly ranging from 1.3 Pa to 1300 Pa (0.01 to 10 mm Hg).

The term "non-volatile oil" herein denotes an oil remaining on the keratinic material such as skin at room temperature and atmospheric pressure for at least several hours and particularly having a vapor pressure less than $10^{-3}$ mm Hg (0.13 Pa).

The oil may be chosen from all physiologically acceptable and particularly cosmetically acceptable oils, in particular mineral, animal, plant, synthetic oils; in particular, volatile or non-volatile hydrocarbon and/or silicone and/or fluorinated oils and mixtures thereof.

More specifically, the term "hydrocarbon oil" denotes an oil mainly comprising carbon and hydrogen atoms and optionally one or several functions chosen from hydroxyl, ester, ether, carboxylic functions. Generally, the oil has a viscosity of 0.5 to 100,000 mPa·s, preferably from 50 to 50,000 mPa·s and more preferably from 100 to 300,000 mPa·s.

By way of examples of volatile oils suitable for use in the invention, mention may be made of:
volatile hydrocarbon oils chosen among hydrocarbon oils having 8 to 16 carbon atoms, and particularly $C_8$-$C_{16}$ isoalkanes originating from crude oil (also called isoparaffins).

By way of examples of non-volatile oils suitable for use in the invention, mention may be made of:
hydrocarbon plant oils such as liquid triglycerides of fatty acids with 4 to 24 carbon atoms such as triglycerides of caprylic/capric acids such as those sold by the Stearineries Dubois Company or those sold under the names Miglyol 810, 812 and 818 by the Dynamit Nobel Company, jojoba oil;

linear or branched hydrocarbons of mineral or synthetic origin, such as paraffin oils and derivatives thereof, petroleum jelly, polydecenes, polybutenes, hydrogenated polyisobutene such as Parleam, squalane;

synthetic ethers having from 10 to 40 carbon atoms;

synthetic esters such as isononyl isononanoate, isopropyl myristate, isopropyl palmitate, $C_{12}$ to $C_{15}$ alcohol benzoate silicone oils such as non-volatile polydimethylsiloxanes (PDMS), either linear (dimethicones) or cyclic (cyclomethicones).

The compositions according to the invention may further comprise one or several cosmetic additives chosen among softeners, opacifiers, stabilizers, preservatives, perfumes, a fatty phase structuring agent chosen particularly from waxes, pasty compounds, gelling agents; organic or inorganic fillers; thickening or suspension agents, or any other ingredient conventionally used in cosmetics for this type of application.

Obviously, the skilled person will take care to choose such optional compound(s) in such a way that the advantageous properties intrinsically associated with the composition according to the invention are not altered, or are not substantially altered, by the envisaged additive(s).

These optional additives may be present in the composition at 0.001 to 80% by weight, in particular from 0.1 to 40% by weight, with respect to the total weight of the composition.

These additives, depending on their nature, may be introduced in the fatty phase or in the aqueous phase of the composition, or in lipid vesicles. In any case, these additives and their proportions shall be chosen by the skilled person such that the advantageous properties of the mixture according to the invention are not altered or not substantially altered by the envisaged additives.

As hydrophilic gelling or thickening agents, mention may be made of carboxyvinylic polymers such as carbomer, acrylic copolymers such as acrylate/alkylacrylate copolymers, polyacrylamides such as the mixture of polyacrylamide, C13-14-isoparaffin and Laureth-7 sold under the name Sepigel 305$^e$ by SEPPIC, polysaccharides such as cellulose derivatives (for example hydroxyalkylcellu loses, particularly hydroxypropylcellulose and hydroxyethylcellulose), natural gums such as guar, carob and xanthan, and clays; as gelling agents or liphophilic thickeners, mention may be made of modified clays such as bentones, metal salts of fatty acids, hydrophobic silica, ethylcellulose and polyethylene.

The composition according to the invention may further comprise other active constituents such as desquamating agents, depigmenting or propigmenting agents, anti-glycation agents, anti-inflammation or soothing agents, agents that stimulate the synthesis of dermal or epidermal macromolecules and/or prevent their degradation, agents that stimulate the proliferation of fibroblasts and/or keratinocytes or that stimulate differentiation of keratinocytes, dermo-relaxing agents, tensor agents, agents acting on microcirculation, agents acting on the energy metabolism of cells, UV filters, odor absorbing agents, or mixtures thereof.

When the composition is an emulsion, the proportion of the fatty phase may be between 5 and 80% by weight, preferably between 8 and 50% by weight relative to the total weight of the composition. The emulsifier and the co-emulsifier may be present in a proportion ranging from 0.3% to 30% by weight, preferably from 0.5% to 20% by weight, relative to the total weight of the composition.

The composition according to the invention can be more or less fluid and have the appearance of a white or colored cream, of an ointment, of a milk, of a lotion, of a serum, of a paste, of a gel or of a foam. It can possibly by applied in the form of an aerosol. It can also be in solid form, particularly in the form of a stick. It can also be on a support, for example on wipes such as makeup removal wipes.

The composition according to the invention may form a skin care composition, particularly a cleaning, protection, treatment or care cream for the face, hands or body, such as day creams, night creams, makeup removal creams, foundation creams, sunscreen creams, makeup removal milk, a body protection or care milk, a sunscreen milk, a lotion, gel or foam for skin care such as a makeup lotion.

The composition according to the invention may advantageously be in the form of a care composition, particularly a moisturizing composition.

In one particular embodiment, the composition according to the invention is in the form of a care composition for dry skins.

The composition according to the invention may also be a makeup composition, and particularly a foundation.

The invention also relates to a non-therapeutic cosmetic treatment method comprising the application of a mixture of arthrofactins as defined above as active ingredient, or a composition according to the invention comprising this mixture of arthrofactins as active ingredient, onto keratinic materials, particularly the skin.

In particular, the cosmetic treatment method according to the invention is for the treatment of keratinic materials, particularly the skin, especially dry skin, and more particularly dry human skin.

Thus, in one particular embodiment, the cosmetic treatment method according to the invention comprises application of the mixture of arthrofactins or the composition containing this mixture on dry skin, particularly on face skin, especially on the forehead and/or neck, and/or on the skin of the hands or feet.

This invention also relates to non-therapeutic cosmetic use of a mixture of arthrofactins as defined above, as moisturizer for keratinic materials, particularly the skin, mucosa and/or keratinic fibers, preferably the skin, even more preferably dry skin.

The inventors have shown that the mixture of arthrofactins according to the invention activated genes associated with moisturization in keratinocytes and therefore had an important moisturizing power.

Thus, in one particular embodiment, the composition according to the invention is used to prevent and/or to treat states of dryness of the skin and/or signs associated with dryness of the skin, such as skins with a rough visual appearance or rough texture to the touch, discomforts such as itching and/or tightness associated with dry skin. In particular, the composition according to the invention can be used to improve moisturization of the skin.

In one particular embodiment, the composition according to the invention is used to treat constitutional non-pathological dry skins or acquired non-pathological dry skins.

Constitutional non-pathological dry skins are dry skins for which the severity can depend on external factors, such as exposure to chemicals, severe weather conditions or solar radiation. This skin category includes senile skin (characterized by a general reduction of skin metabolism with age) and fragile skin.

Acquired non-pathological dry skins are skins for which dryness is induced by the external factors mentions above.

The expressions "comprised between . . . and . . . " and "ranging from . . . to . . . ", or "at least . . . " must be understood as including the limits, unless mentioned otherwise.

Throughout the following, percentages are given by weight unless mentioned otherwise.

The following examples illustrate the invention, and are given purely for illustrative and non-limitative purposes.

EXAMPLES

Example 1

The MIS38 strain was cultivated in a King'B medium at 28° C., 120 rpm and 4 vvm. At the end of fermentation, the culture medium was clarified by centrifuging and the supernatant obtained was concentrated by ultrafiltration (MWCO 10 kDa). Control of the transmembrane pressure within an appropriate concentration interval makes it possible to measure a concentration 7 times higher in the supernatant, that is then diafiltered twice to eliminate residual contamination in the culture medium. This fraction is then dry concentrated until obtaining a dry powder.

Example 2.1: The Mixture of Arthrofactins According to the Invention has a Moisturizing Power This example shows that the mixture of arthrofactins according to the invention activates the genes associated with hydration, in transcriptome, in keratinocytes.

K266 human epidermic keratinocytes were seeded in wells (50,000 cells/well) and cultivated in a Dermalife K medium (Lifeline LL-007) for 3 days at 37° C. and 5% of $CO_2$. At the end of incubation, the culture medium was replaced by a test medium (K Dermalife supplemented with 1.5 mM $CaCl_2$) containing or not containing (control) the mixture of arthrofactins obtained in example 1 in the form of a powder diluted to 0.1% in water or references (retinoic acid at 0.1 µM and 1 µM, or retinol at 10 µM). The cells were then incubated for 24 hours.

In parallel, normal human keratinocytes (NHK, 01.12) were seeded in wells (50,000 cells/well) and cultivated in a COMPLETE KGM medium (KGM BULLETKIT, LONZA, CC-3111) for 3 days at 37° C. and 5% of $CO_2$. At the end of incubation, the culture medium was replaced by a test medium (KGM supplemented with 1.5 mM $CaCl_2$) containing or not containing (control) the mixture of arthrofactins described in example 1 or the references (retinoic acid at 0.1 µM and 1 µM, or retinol at 10 µM). The cells were then incubated for 24 hours.

References such as 0.1 µM and 1 µM retinoic acid, or retinol at 10 µM are used as global controls of good keratinocyte response.

At the end of the treatment, the culture media were eliminated, the cells were rinsed twice with PBS (w/o $CaCl_2$, w/o $MgCl_2$) before being lysed. Wells of the same condition were regrouped in pairs, and RNA was then extracted by magnetic beads using the Ambion isolation kit: MagMAX™-96 Total RNA Isolation Kit, reference AM1830.

The quantification of RNA and quality control were analyzed using LabChip GX (Perkin Elmer). Reverse transcription (RT) of RNA into cDNA was carried out using the Quantitect® inverse transcription kit (QIAGEN) following the manufacturer's recommendations. For this step, RNA was diluted to 1 µg/ml in RNase-free water based on the sample of each concentration of RNA.

After elimination of genomic DNA, the samples were mixed with the Master Mix (Quantiscript Reverse Transcriptase, Quantiscript RT Buffer and RT Primer Mix) and then incubated at 42° C. for 15 minutes before being inactivated at 95° C.

The expression of selected transcripts was then analyzed by quantitative PCR using a LightCycler 480 Real-Time PCR System 384-well plate system (Roche) using the SYBR® Green incorporation technique (Roche).

It is observed that the mixture of arthrofactins of example 1 at 0.002 mg/L and 0.01 mg/L in water strongly activates genes associated with moisturization in keratinocytes cultivated in vitro.

Under these conditions, the arthrofactin tested at 0.01 mg/mL stimulated the expression of markers involved in creation of the corneal layer (TGM5, LCE3D, FLG2, SPRR1A, CNFN, ELOVL3) and the transport of solutes (AQP9). This reinforcement of the corneal layer enables limiting water losses and therefore ultimately improves moisturization of the epidermis. Furthermore, stimulation of the expression of SCNN1A and SCNN1D was also observed. These two markers are involved in the regulation of ENaC, that is a sodium channel that plays a role in the regulation of hydric flows of the epidermis.

Example 2.2: Comparative Example Outside the Scope of the Invention: Test of the Power Capacity of Surfactin This example shows that surfactin (compound outside the scope of the invention) leads to a lower expression of genes associated with moisturization, in transcriptome, in keratinocytes, than the expression induced by the mixture of arthrofactins according to example 1.

K266 human epidermic keratinocytes were seeded in wells (50,000 cells/well) and cultivated in a Dermalife K medium (Lifeline LL-007) for 3 days at 37° C. and 5% of $CO_2$. At the end of incubation, the culture medium was replaced by a test medium (K Dermalife supplemented with 1.5 mM $CaCl_2$) containing or not containing (control) surfactin in the form of a sodium salt (Aminofect marketed by KANEKA) diluted to 0.1% in water or references (retinoic acid at 0.1 µM and 1 µM, or retinol at 10 µM). The cells were then incubated for 24 hours.

In parallel, normal human keratinocytes (NHK, 01.12) were seeded in wells (50,000 cells/well) and cultivated in a COMPLETE KGM medium (KGM BULLETKIT, LONZA, CC-3111) for 3 days at 37° C. and 5% of $CO_2$. At the end of incubation, the culture medium was replaced by a test medium (KGM supplemented with 1.5 mM $CaCl_2$) containing or not containing (control) surfactin in the form of a sodium salt (Aminofect marketed by KANEKA) diluted to 0.1% in water or the references (retinoic acid at 0.1 µM and 1 µM, or retinol at 10 µM). The cells were then incubated for 24 hours.

References such as 0.1 µM and 1 µM retinoic acid, or retinol at 10 µM are used as global controls of good keratinocyte response.

The expression of selected transcripts was then analyzed by quantitative PCR using a LightCycler 480 Real-Time PCR System 384-well plate system (Roche) using the SYBR® Green incorporation technique (Roche).

It is observed that surfactin at 0.002 mg/L and 0.01 mg/L in water leads to a lower expression of genes associated with moisturization in keratinocytes cultivated in vitro than the expression induced by the mixture of arthrofactins according to example 1 for the same concentrations, as shown in Table 1. The markers for which the expression is measured are particularly involved in the constitution of the corneal layer (TGM5, LCE3D, FLG2, SPRR1A, CNFN, ELOVL3), transport of solutes (AQP9), and markers involved in regulation of ENaC (SCNN1A and SCNN1D).

TABLE 1

| | | Compound tested | | | |
|---|---|---|---|---|---|
| Level of expression of moisturization markers* | | Mixture of arthrofactins at 0.002 mg/L (according to the invention example 1) | Sodium Surfactin at 0.002 mg/L (outside invention) | Mixture of arthrofactins at 0.01 mg/L (according to the invention example 1) | Sodium Surfactin at 0.01 mg/L (outside invention) |
| Group I markers involved in constitution of the corneal layer | TGM5, LCE3D, FLG2, SPRR1A, CNFN, ELOVL3 | ++ | − | ++++ | + |
| Group II Marker involved in the transport of solutes | AQP9 | + | − | +++ | − |
| Group III markers involved in the regulation of ENaC | SCNN1A SCNN1D | ++ | − | +++ | − |

*expression levels are presented in the form of an average value per group of biomarkers.

At the end of the treatment, the culture media were eliminated, cells were rinsed twice with PBS (w/o $CaCl_2$, w/o $MgCl_2$) before being lysed. Wells of the same condition were regrouped in pairs, and RNA was then extracted by magnetic beads using the Ambion isolation kit: Mag-MAX™-96 Total RNA Isolation Kit, reference AM1830.

The quantification of RNA and quality control were analyzed using LabChip GX (Perkin Elmer). Reverse transcription (RT) of RNA into cDNA was carried out using the Quantitect® inverse transcription kit (QIAGEN) following the manufacturer's recommendations. For this step, RNA was diluted to 1 µg/ml in RNase-free water based on the sample of each concentration of RNA.

After elimination of genomic DNA, the samples were mixed with the Master Mix (Quantiscript Reverse Transcriptase, Quantiscript RT Buffer and RT Primer Mix) and then incubated at 42° C. for 15 minutes before being inactivated at 95° C.

Example 3: Compositions for Topical Application

| | % by weight |
|---|---|
| Compound according to example 1 | 4% |
| Glycerol monostearate | 0.8% |
| Cetyl alcohol | 2.0% |
| Stearyl alcohol | 5.0% |
| Polyoxyethylene stearate (20 OE) | 3.0% |
| Cross-linked acrylic acid (CARBOPOL 941) | 0.3% |
| Caprylic/capric triglycerides | 12.0% |
| Preservatives q.s. | |
| Water qsp | 100.0% |

The exemplified cosmetic formulation applied on the skin shows a good skin moisturization effect.

Example 4: Other Compositions for Topical Application

|  | % by weight |
| --- | --- |
| Compound according to example 1 | 4% |
| Cross-linked acrylic acid (CARBOPOL 941) | 0.3% |
| Preservatives q.s. | |
| Water qsp | 100.0% |

The exemplified cosmetic formulation applied on the skin shows a good skin moisturization effect.

The invention claimed is:

1. A cosmetic composition comprising as an active ingredient a mixture of arthrofactins comprising (i) arthrofactin A of the following formula (I):

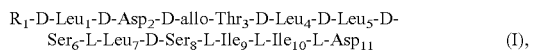

(I), wherein the hydroxyl group of the D-allo-Thr$_3$ amino acid residue forms an ester bond with the C-terminal carboxyl group of the L-Asp$_{11}$ amino acid residue, and R$_1$ represents the group of the following formula (I'):

(I')

wherein R$_1$' is a saturated alkyl chain with 5 to 8 carbon atoms, and (ii) at least one derivative of arthrofactin A, said derivative is selected from the group consisting of arthrofactin B, arthrofactin C, arthrofactin D and mixtures thereof, (a) arthrofactin B being of the following formula (III):

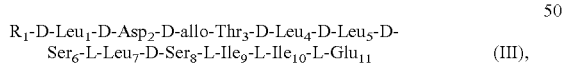

(III), wherein the hydroxyl group of the D-allo-Thr$_3$ amino acid residue forms an ester bond with the C-terminal carboxyl group of the L-Glu$_{11}$ amino acid residue, and R$_1$ represents the group of the following formula (I'):

(I')

wherein R$_1$' is a saturated alkyl chain with 5 to 8 carbon atoms;

(b) arthrofactin C being of the following (IV):

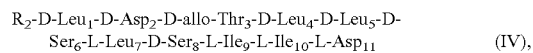

(IV), wherein the hydroxyl group of the D-allo-Thr$_3$ amino acid residue forms an ester bond with the carboxyl C-terminal group of the L-Asp$_{11}$ amino acid residue, and R$_2$ represents the group of the following formula (IV'):

(IV')

wherein R$_2$' is an alkyl chain with 9 carbon atoms, comprising exactly one unsaturation;

(c) arthrofactin D being of the following formula (V):

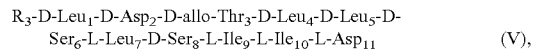

(V), wherein the hydroxyl group of the D-allo-Thr$_3$ amino acid residue forms an ester bond with the C-terminal carboxyl group of the L-Asp$_{11}$ amino acid residue, and R$_3$ represents the group of the following formula (V'):

(V')

wherein R$_3$' is a saturated alkyl chain with 9 carbon atoms;

the composition further comprising a physiologically acceptable medium; wherein the amount of the mixture of arthrofactins is between 0.01 and 10% by weight based upon the weight of the composition and the composition is in the form of an emulsion, a cream, an ointment, a milk, a lotion, a serum, a paste, a gel, a foam or a stick.

2. The composition according to claim 1, wherein R$_1$' is a saturated alkyl chain with 7 carbon atoms.

3. The composition according to claim 1, wherein said mixture of arthrofactins comprises:
(i) arthrofactin A of the following formula (IA):

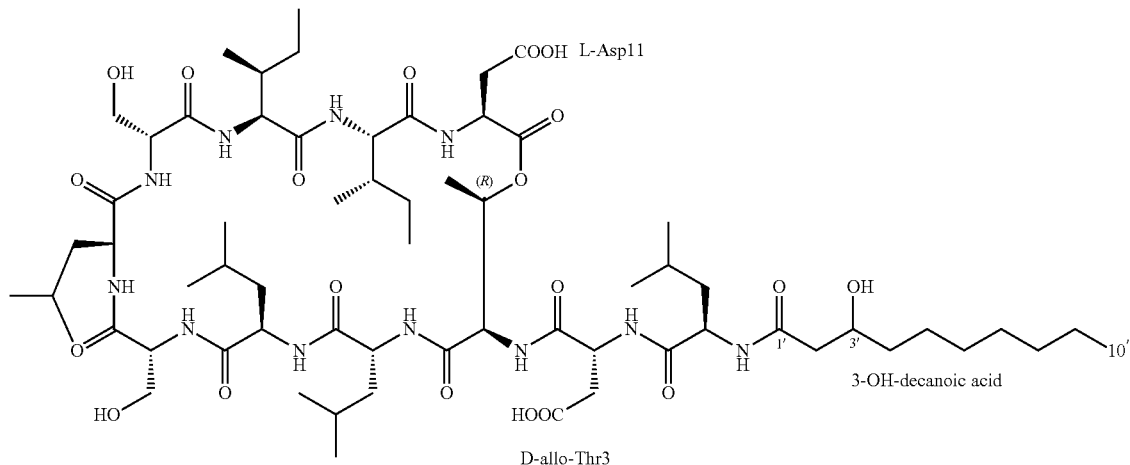

and

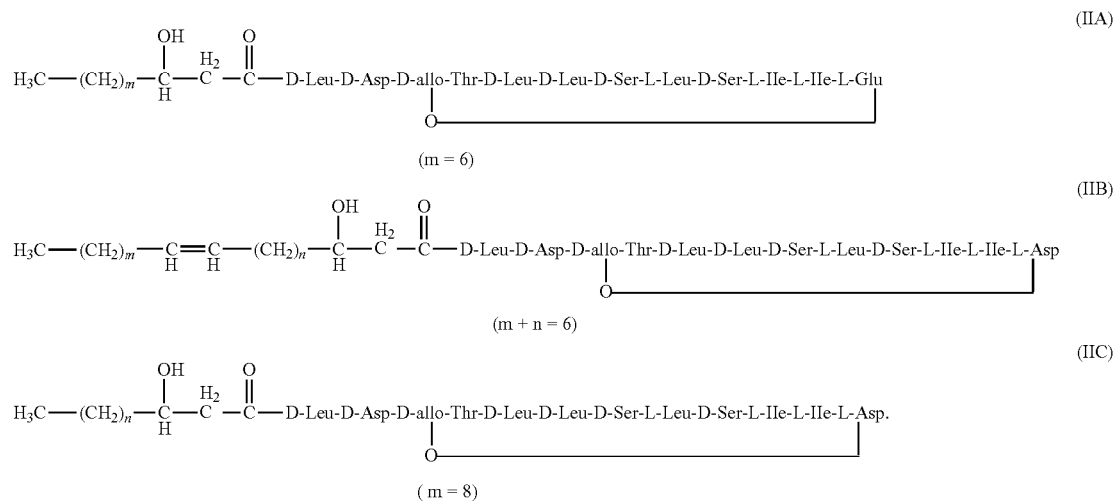

4. The composition according to claim 3, wherein said at least one derivative of arthrofactin A is a mixture of said compounds of formulas (IIA), (IIB) and (IIC).

5. The composition according to claim 1, wherein said mixture of arthrofactins mostly comprises arthrofactin A.

6. The composition according to claim 1, wherein said mixture of arthrofactins is obtained by fermentation with the *Pseudomonas* sp. strain MIS38.

7. The composition according to claim 1, wherein the composition is in form of a care composition.

8. The composition according to claim 1, wherein the composition further comprises at least one compound selected from softeners, opacifiers, stabilizers, preservatives, perfumes, a fatty phase structuring agent; organic or inorganic fillers; thickening or suspension agents.

9. The composition according to claim 1, comprising the mixture of arthrofactins as an active agent for moisturizing keratinic materials.

10. A method for non-therapeutic cosmetic treatment which comprises applying the composition as defined in claim 1, on the skin.

11. The method according to claim 10, the method comprising applying the composition as defined in claim 1 to the skin, wherein the skin is a dry skin.

12. A non-therapeutic cosmetic treatment for moisturizing keratinic material which comprises applying the composition of claim 1 to said keratinic material.

13. A method for non-therapeutic cosmetic treatment which comprises applying the composition as defined in claim 2, on the skin.

14. A method for non-therapeutic cosmetic treatment which comprises applying the composition as defined in claim 3, on the skin.

15. A method for non-therapeutic cosmetic treatment which comprises applying the composition as defined in claim 3, on the skin.

16. A method for non-therapeutic cosmetic treatment which comprises applying the composition as defined in claim 5, on the skin.

* * * * *